(12) United States Patent
Suzuki et al.

(10) Patent No.: US 6,376,740 B1
(45) Date of Patent: *Apr. 23, 2002

(54) DISPOSABLE DIAPER

(75) Inventors: Naomi Suzuki; Makoto Suekane, both of Kagawa-ken (JP)

(73) Assignee: Uni-Charm Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,535

(22) Filed: Mar. 30, 1999

(30) Foreign Application Priority Data

Mar. 31, 1998 (JP) .......................... 10-087391

(51) Int. Cl.$^7$ ................................ A61F 13/15
(52) U.S. Cl. .................. 604/358; 604/385.01
(58) Field of Search .................. 604/385.1, 385.2, 604/385.01, 385.02, 358, 386, 540, 385.03

(56) References Cited

U.S. PATENT DOCUMENTS

| | | | |
|---|---|---|---|
| 4,018,226 A | * | 4/1977 | Korgemets ................ 604/392 |
| 5,074,854 A | | 12/1991 | Davis |
| 5,383,871 A | * | 1/1995 | Carlin et al. |
| 5,397,379 A | * | 3/1995 | Barker et al. ................ 75/319 |
| H1440 H | * | 5/1995 | New et al. .................... 604/386 |
| 5,549,775 A | * | 8/1996 | Odorzynski ................ 156/227 |
| 5,558,658 A | * | 9/1996 | Menard et al. .......... 604/385.1 |
| 5,634,916 A | * | 6/1997 | Lavon et al. ............. 604/385.1 |

FOREIGN PATENT DOCUMENTS

| WO | WO 91/08725 | 6/1991 |
|---|---|---|
| WO | WO 96/08224 | 3/1996 |
| WO | WO 96/19169 | 6/1996 |

* cited by examiner

Primary Examiner—Sharon Kennedy
Assistant Examiner—Kevin C. Sirmons
(74) Attorney, Agent, or Firm—Baker & Daniels

(57) ABSTRACT

A disposable diaper has a first section forming a part of a front waist region and a second section forming the remaining part of the diaper. The first and second sections are joined together over the entire width of the diaper along a joined zone extending over the entire width of the diaper so that the joined zone describes a concave line from the front waist region towards a rear waist region as the first section is folded back onto the second section with respective outer surfaces of these first and second sections facing each other. The diaper thus formed fitting thereof to a wearer's belly.

9 Claims, 3 Drawing Sheets

DISPOSABLE DIAPER

BACKGROUND OF THE INVENTION

The present invention relates to a disposable diaper and more particularly, a disposable diaper including front and rear waist regions adapted to be separably joined together along their transversely opposite side edges when the diaper is put on a wearer's body.

Such a type disposable diaper is relatively flat before its actual use and includes a liquid-pervious topsheet, a liquid-impervious backsheet and a liquid-absorbent core disposed between these two sheets. The diaper is usually provided along its waist-opening and its leg-openings with elastic members secured under appropriate tension to a component of the diaper so that the diaper may fit to a wearer's body under contraction of these elastic members.

However, it has been difficult to put such a flat diaper on the wearer's body in conformity with a convex trunk of the wearer (bulge of the wearer's belly) without leaving gaps between the diaper and the wearer's skin. Such gaps will cause body fluids to leak along these gaps. If the number of gaps is too many, the diaper will become too baggy to follow the movement of the wearer's body and create a feeling of discomfort against the wearer.

SUMMARY OF THE INVENTION

In view of the above problem, it is an object of the present invention to provide a disposable diaper improving fitting of the front waist region to the wearer's skin.

According to the present invention, there is provided a disposable diaper having a front waist region, a rear waist region and a crotch region extending therebetween, the diaper including a first section forming a part of the front waist region inclusive of a front end thereof and a second section forming the remaining part of the diaper and joined to the first section over the entire width of the diaper along a joint zone extending over the entire width of the diaper so that the joined zone describes a concave line toward a rear end of the rear waist region when the first section is folded back onto the second section with respective outer surfaces of the first and second sections facing each other.

The present invention can further include embodiments: the front and rear region being adapted to be separately joined together along their transversely opposite side edges when the diaper is put on a wearer's body; the first section being formed by a liquid-impervious sheet and the second section is formed by a liquid-pervious topsheet, a liquid-impervious backsheet and a liquid-absorbent core disposed therebetween so that an outer surface of the liquid-impervious backsheet forming the first section is joined to an outer surface of the backsheet forming the second section along the joined zone; the first section being formed by a nonwoven fabric; the first section being formed by a sheet elastically stretchable and contractable transversely of the diaper; the joined zone being water-tight; and the first section being formed separately from the second section and joined to the second section by means of any of adhesion, heat-sealing and stitching.

With the disposable diaper according to the present invention, the front waist region is adapted to swell forward of the diaper in proximity of the joined zone longitudinally dividing the front waist region in two. Such a unique arrangement advantageously enables the front waist region to fit to the wearer's belly so that not only undesirable leakage of body fluids can be reliably prevented but also a feeling to wear the diaper can be improved.

DETAILED DESCRIPTION OF THE PREFERRED EMBODIMENTS

Details of a disposable diaper according to the present invention will be more fully understood from the description given hereunder with respect to the accompanying drawings.

Figure 1:
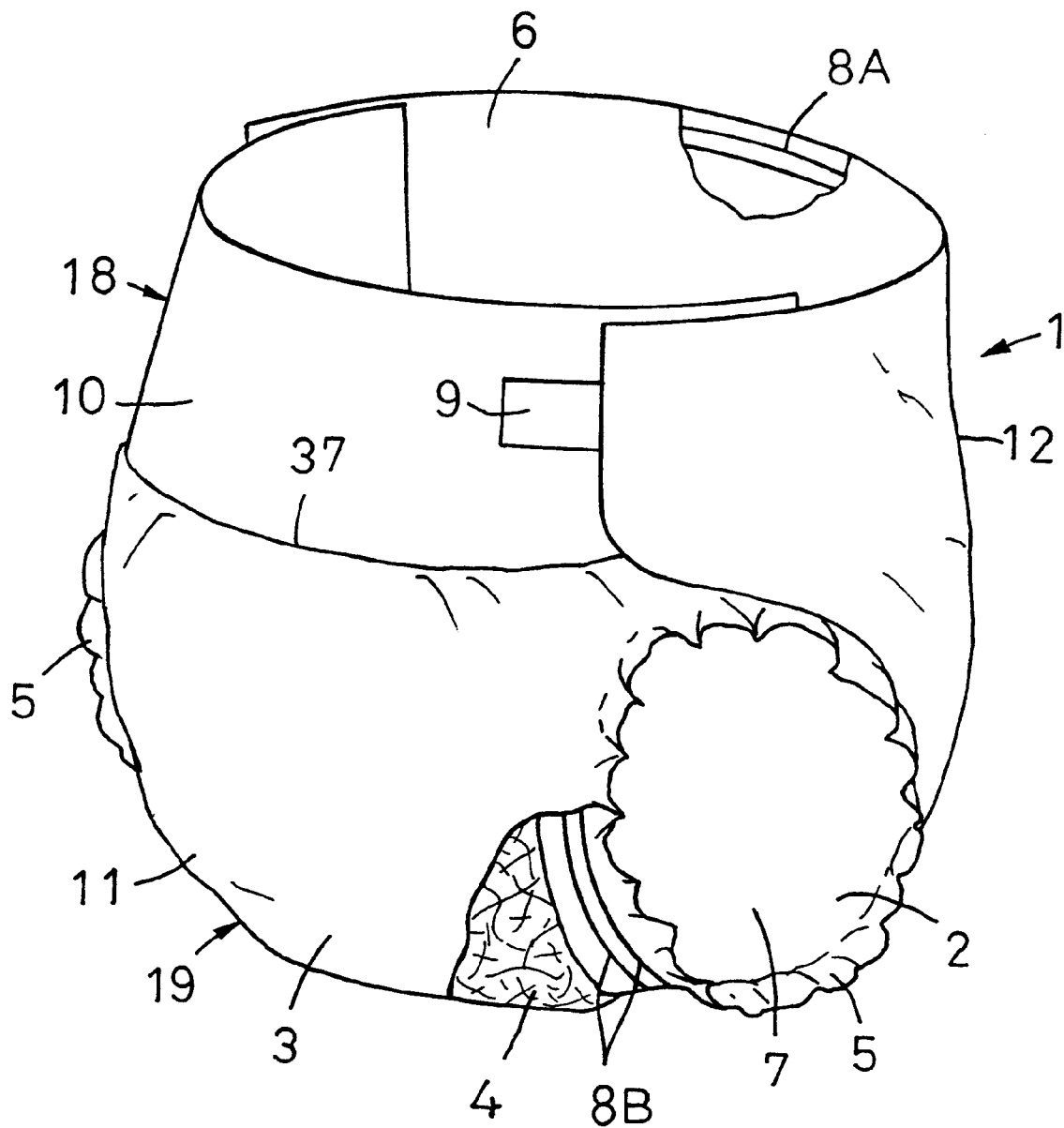
FIG. 1 is a perspective view of a disposable diaper constructed according to one embodiment of the present invention in its state put on a wearer's body.
Figure 2:
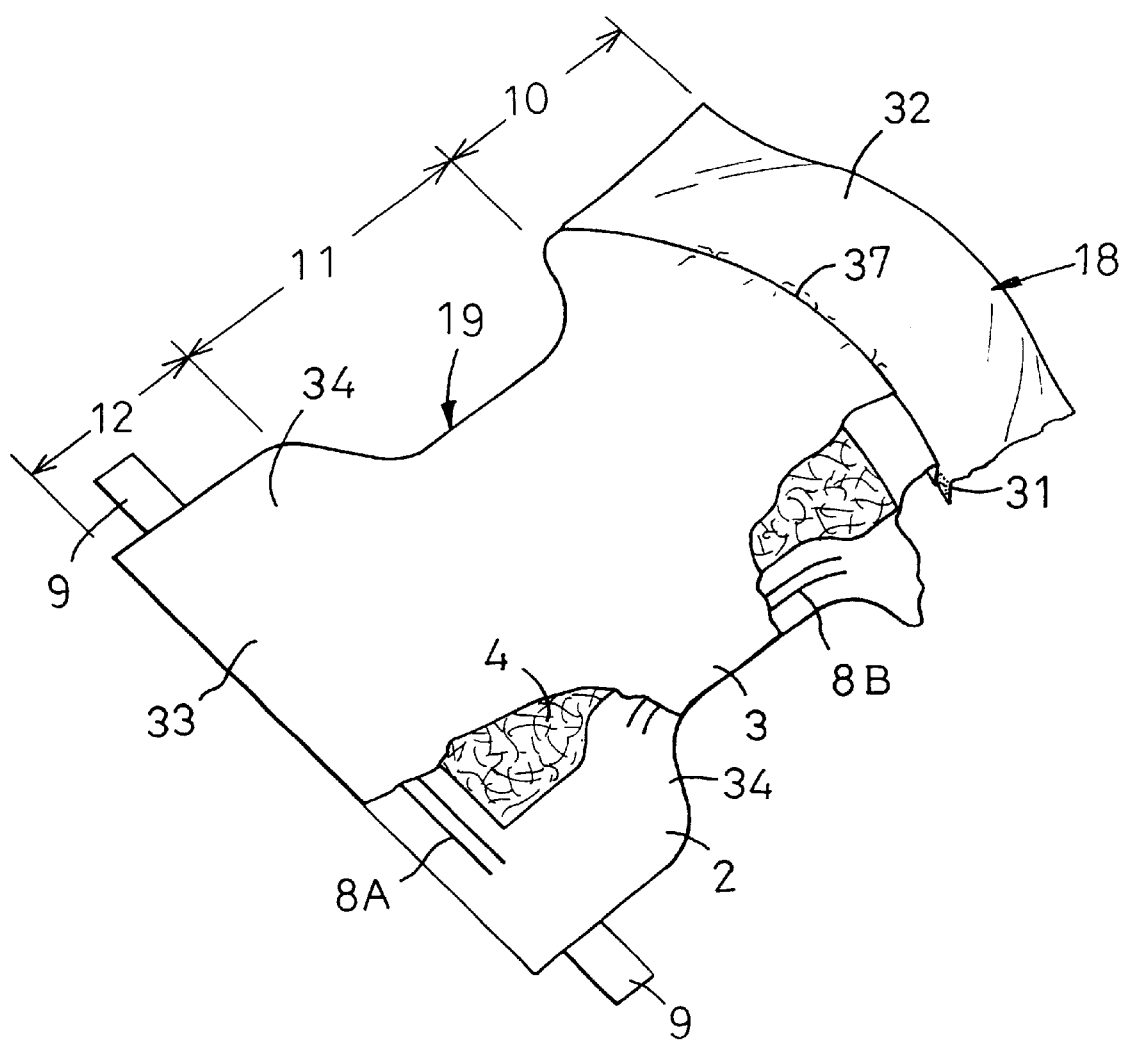
FIG. 2 is a perspective view of the disposable diaper as developed in a longitudinal direction of the diaper.

FIG. 1 is a perspective view of a disposable diaper 1 in its state put on a wearer's body as partially broken away and FIG. 2 is a perspective view of the diaper 1 placed on a plane with its inner side facing downwards. The diaper 1 is longitudinally configured with a front waist region 10, a rear waist region 12 and a crotch region 11 extending between these two waist regions 10, 12. The front waist region 10 comprises, in turn, a first section 18 as a part of the front waist region 10 and a second section 19 as the remainder of the front waist region 10 wherein these two sections are joined together along a joined zone 31 extending transversely of the diaper 1. Peripheries of the diaper 1 is defined by longitudinally opposite ends 32, 33 and transversely opposite side edges 34, 34. Transversely opposite side edges 34 of the rear waist region 12 are provided with tape fasteners 9, respectively, adapted to be separably anchored on an outer surface of the front waist region 10 when the diaper 1 is put on the wearer's body. FIG. 1 shows the diaper 1 as it is put on the wearer's body and a waist-opening 6 as well as a pair of leg-openings 7 are formed.

The first section 18 of the diaper 1 is made of a sheet material, preferably of a nonwoven fabric or a laminated sheet consisting of a nonwoven fabric and a plastic film, more preferably of a stretchable and contractable nonwoven fabric or a laminated sheet consisting of such a stretchable and contractable nonwoven fabric and a stretchable and contractable plastic film. The stretchable and contractable sheet of any kind is used so that such sheet is stretchable and contractable circumferentially of the waist region. In the case of the laminated sheet consisting of a nonwoven fabric and a plastic film, the laminated sheet is used with the nonwoven fabric lying inside.

The second section 19 of the diaper 1 includes the liquid-pervious topsheet 2, the liquid-impervious backsheet 3 and the liquid-absorbent core 4 disposed between these two sheets 2, 3. The topsheet 2 and the backsheet 3 extend outwards beyond peripheral edges of the core 4 so as to be placed one upon another and bonded together along these extensions. Along transversely opposite side edges 34 of the crotch region 11 in the second section 19, elastic members 8B extend longitudinally of the diaper 1, describing a curve. These elastic members 8B are disposed between the topsheet 2 and the backsheet 3 and secured under appropriate tension to a inner surface of at least one of these two sheets 2, 3.

Figure 3:
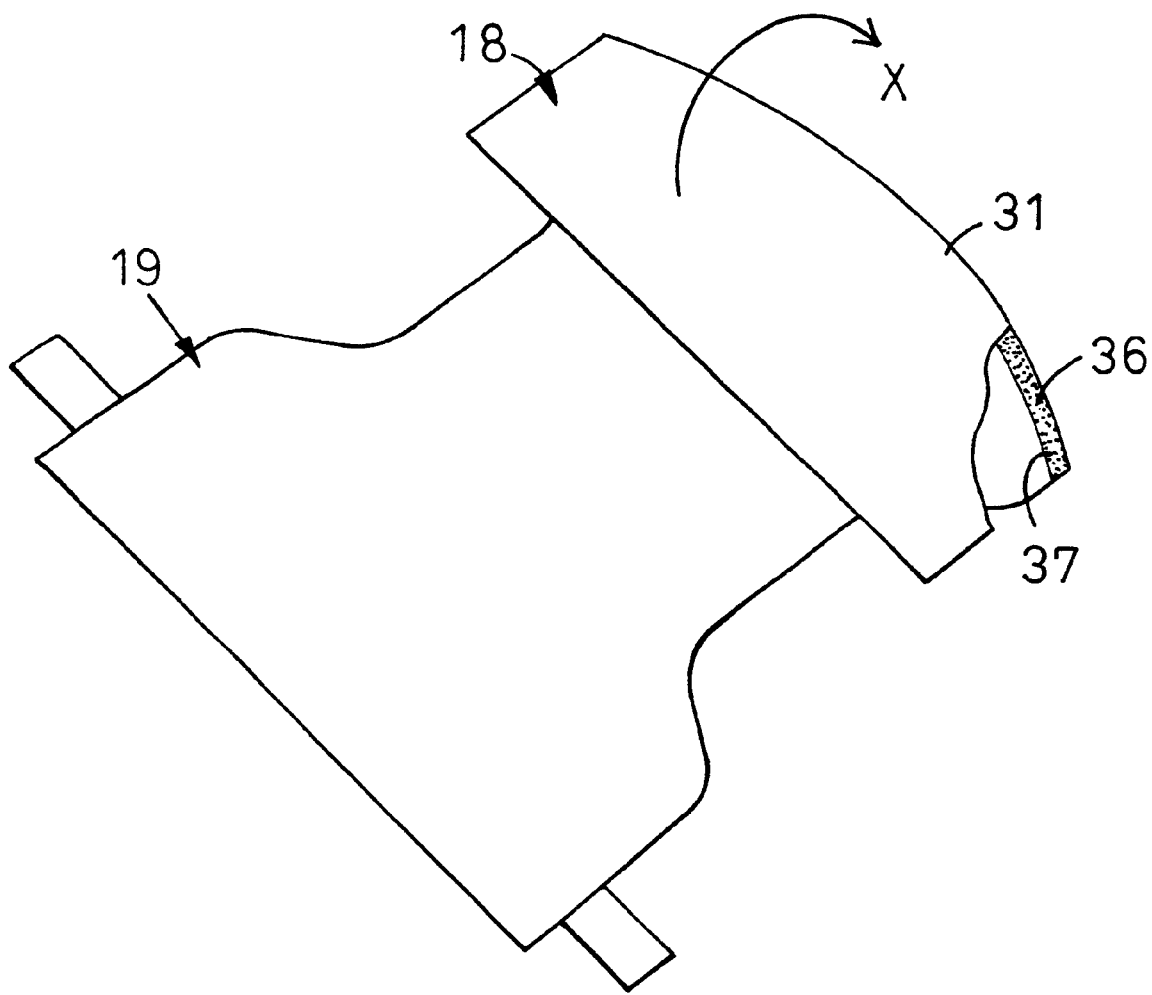
FIG. 3 is a perspective view of the disposable diaper with a first section folded back onto a second section as partially broken away.

FIG. 3 is a perspective view partially broken away of the diaper 1, illustrating a manner in which the first and second sections are joined to each other. The diaper 1 is shown herein as developed longitudinally as well as transversely with both an elastic member 8A associated with the waist-opening and the elastic members 8B associated with the leg-openings being under tension. As shown, the first section 18 is folded back along the joining line onto the second section 19 so that an outer surface of the first section 18 is placed upon an outer surface of the second section 19. Along the joined zone 31 also, the outer surface of the first section 18 is placed upon the outer surface of the second section 19 and these outer surfaces are joined together by means of adhesive 36 applied on one of these outer surfaces so as to describe a concave line toward a rear end of the rear waist region 12 of the diaper 1. Expression used herein "so as to describe a concave line" means that an edge 37 of the joined zone 31 applied with the adhesive 36 which extends adjacent the outer surface of the diaper 1 is concavely curved toward the rear end of the rear waist region 12. The first section 18 joined to the remaining section 19 in this manner is folded along the joined zone 31 inwardly of the diaper 1 in a direction indicated by an arrow X and at the same time the joined zone 31 is pushed forward from the inner side of the diaper 1 so that the joined zone 31 may round out forward as seen in the diaper 1 shown by FIG. 2. The front waist region 10 rounds out forwardly in proximity of the edge 37 and therefore the inner side of this area rounding out may be tightly placed against a convex belly of a baby to achieve desired fitting of the front waist region 10 substantially without generation of creases in the front waist region 10 after the diaper 1 has been put on the baby's body.

Alternatively, the first section 18 of the diaper 1 can be formed by prolonging the backsheet 3 of the second section 19 forward. In this case, the prolonged section of the backsheet 3 for forming the first section 18 is folded back onto a section of the backsheet 3 for defining the second section 19 so that the outer surface of the prolonged section may be placed upon the outer surface of the section defining the second section 19. Then, these two sections are joined together by suitable means of adhesion, heat-sealing or stitching to form the joined zone 31. Like the second section 19, the first section 18 also may include the liquid-pervious topsheet, the liquid-impervious backsheet and the liquid-absorbent core disposed between these two sheets. In the first section 18 according to such an alternative embodiment, the topsheet 2 and the backsheet 3 are placed one upon another and joined together along their portions extending outwards beyond the peripheral edges of the core. Thereafter, the outer surface of this backsheet section defining the first section 18 may be joined to the outer surface of the backsheet section defining the second section 19.

What is claimed is:

1. A disposable diaper having a front waist region, a rear waist region and a crotch region extending therebetween, said disposable diaper including a first portion which forms a part of said front waist region inclusive of a front end thereof and a second portion which forms a remaining part of said diaper exclusive of the front end, said second portion being joined to said first portion over an entire width of said diaper along a joined zone which is spaced apart from a longitudinal edge of the front end which defines a waist opening when the diaper is worn, said joined zone extending across the entire width of said diaper and describing a concave line which is concave toward a rear end of said rear waist region when said first portion is folded back onto said second portion with respective outer surfaces of the first and second portions facing each other.

2. A disposable diaper according to claim 1, wherein said front and rear waist region are separably joined together along transversely opposite side edges thereof when the diaper is put on a wearer's body.

3. A disposable diaper according to claim 1, wherein said first portion comprises a liquid-pervious sheet and said second portion comprises a liquid-pervious topsheet, a liquid-impervious backsheet and a liquid-absorbent core disposed therebetween so that an outer surface of said liquid-impervious sheet of said first portion is joined to an outer surface of the backsheet of said second portion along said joined zone.

4. A disposable diaper according to claim 1, wherein said first portion comprises a nonwoven fabric.

5. A disposable diaper according to claim 1, wherein said first portion comprises a sheet which is elastically stretchable and contractible transversely of said diaper.

6. A disposable diaper according to claim 1, wherein said joined zone is water-tight.

7. A disposable diaper according to claim 1, wherein said first portion is formed separately from said second portion and is joined to said second portion by adhesion.

8. A disposable diaper according to claim 1, wherein said first portion is formed separately from said second portion and is joined to said second portion by heat-sealing.

9. A disposable diaper according to claim 1, wherein said first portion is formed separately from said second portion and is joined to said second portion by stitching.

* * * * *